United States Patent [19]

Cervos et al.

[11] Patent Number: 5,693,342
[45] Date of Patent: Dec. 2, 1997

[54] COUMARIN SPHERULES/BEADS HAVING UNIQUE MORPHOLOGY

[75] Inventors: Eric Cervos; Pierre Labourt-Ibarre, both of Lyons; Eraclis Statiotis, Villette D'Anthon, all of France

[73] Assignee: Rhone-Poulenc Chimie, Courbevoie Cedex, France

[21] Appl. No.: 405,232

[22] Filed: Mar. 16, 1995

[30] Foreign Application Priority Data

Mar. 16, 1994 [FR] France ..................... 94 03094

[51] Int. Cl.[6] ..................................................... A61K 9/14
[52] U.S. Cl. ........................... 424/489; 424/470; 424/464
[58] Field of Search ............................... 424/489, 488, 424/490, 467, 464; 425/222

[56] References Cited

U.S. PATENT DOCUMENTS

| | | | |
|---|---|---|---|
| 4,946,359 | 8/1990 | Christen | 425/222 |
| 5,260,072 | 11/1993 | Roche et al. | 424/464 |
| 5,283,065 | 2/1994 | Doyon et al. | 424/467 |

*Primary Examiner*—Thurman K. Page
*Assistant Examiner*—William E. Benston, Jr.
*Attorney, Agent, or Firm*—Burns, Doane, Swecker & Mathis, L.L.P.

[57] ABSTRACT

Free-flowing, non-agglomerating and attrition resistant, substantially spherical solid beads/spherules of a coumarin compound, advantageously having a particle size ranging from 100 µm to 2,000 µm, a loose bulk density ranging from 0.25 to 0.8 and a compressive strength ranging from 500 to 10,000 $N/m^2$, dissolve rapidly in ethanol and are conveniently prepared by prilling/fragmenting a melt of the coumarin compound into a stream of a cooling gas.

30 Claims, 6 Drawing Sheets

5,693,342

1

COUMARIN SPHERULES/BEADS HAVING UNIQUE MORPHOLOGY

BACKGROUND OF THE INVENTION

1. Field of the Invention

The present invention relates to a novel morphological form of coumarin and derivatives thereof, and, more especially, to solid spherules of coumarin and/or derivatives thereof.

This invention also relates to a process for the preparation of such coumarin spherules/beads.

2. Description of the Prior Art

Coumarin and derivatives thereof are widely used in the perfume industry. Coumarin also finds application in other fields such as the pharmaceutical industry. Thus, it is a compound that is in great demand.

Coumarin is currently available commercially as a crystalline powder comprising platelike or waferlike crystals. This powder presents the same disadvantages and drawbacks as are encountered when handling any other powder.

SUMMARY OF THE INVENTION

Accordingly, a major object of the present invention is the provision of a novel morphological form of coumarin compounds which does not generate dust, which does not become lumpy or agglomerate during storage and which otherwise avoids or conspicuously ameliorates the aforesaid disadvantages and drawbacks to date characterizing the state of this art.

Another object of this invention is the provision of a novel morphological form of coumarin compounds that exhibits good flowability (free-flowing) and which has an improved dissolution rate in comparison with the prior art forms of coumarin and derivatives thereof.

Briefly, the present invention features spherules or beads of coumarin compounds, namely, solid particulates that are substantially or highly spherical in geometry.

The present invention also features a process for the preparation of such coumarin spherules/beads, comprising melting a coumarin compound, fragmenting or comminuting the melt into droplets, solidifying said droplets, characteristically by permitting same to fall into a stream of a cooling gas and thus solidify, and then recovering the spherules/beads thus formed.

DETAILED DESCRIPTION OF BEST MODE AND PREFERRED EMBODIMENTS OF THE INVENTION

Figure 1:
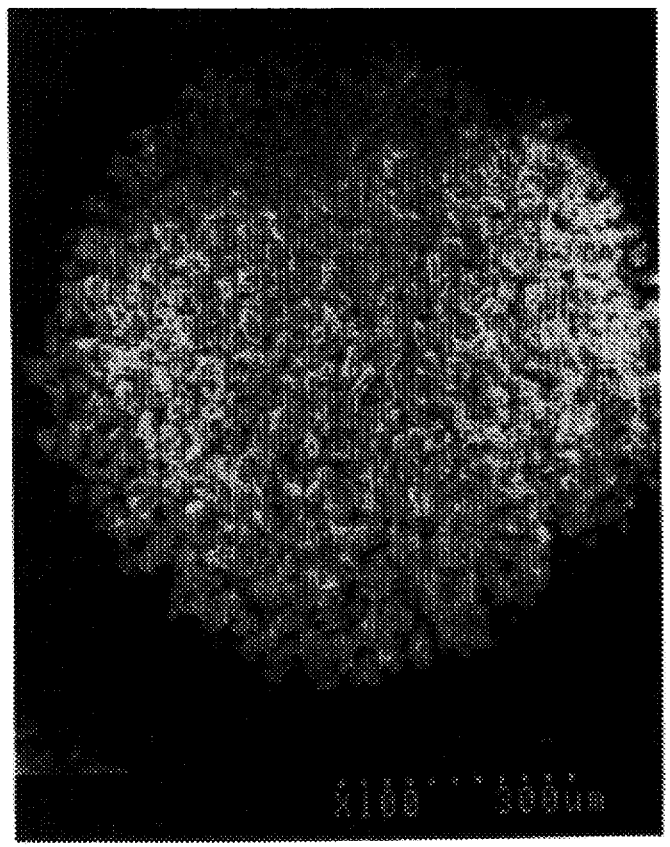
FIGS. 1–5 are scanning electron photomicrographs illustrating the morphology of the solid coumarin spherules/beads of the present invention.
Figure 2:
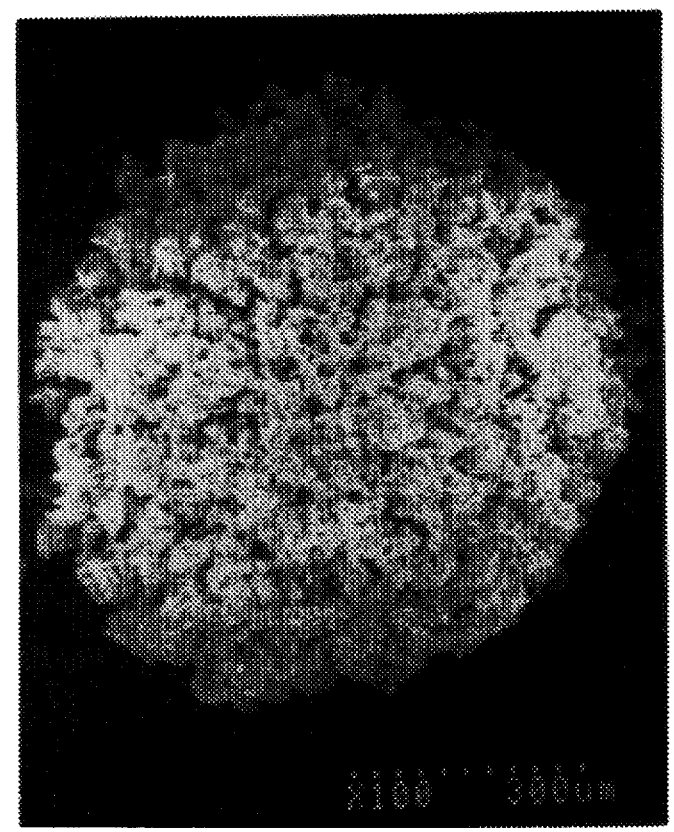
Figure 3:
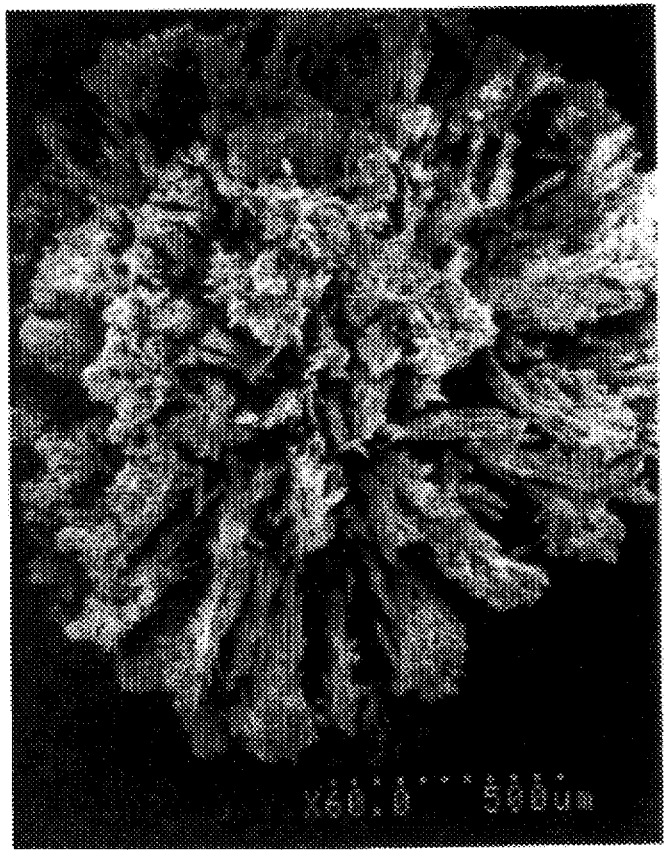
Figure 4:
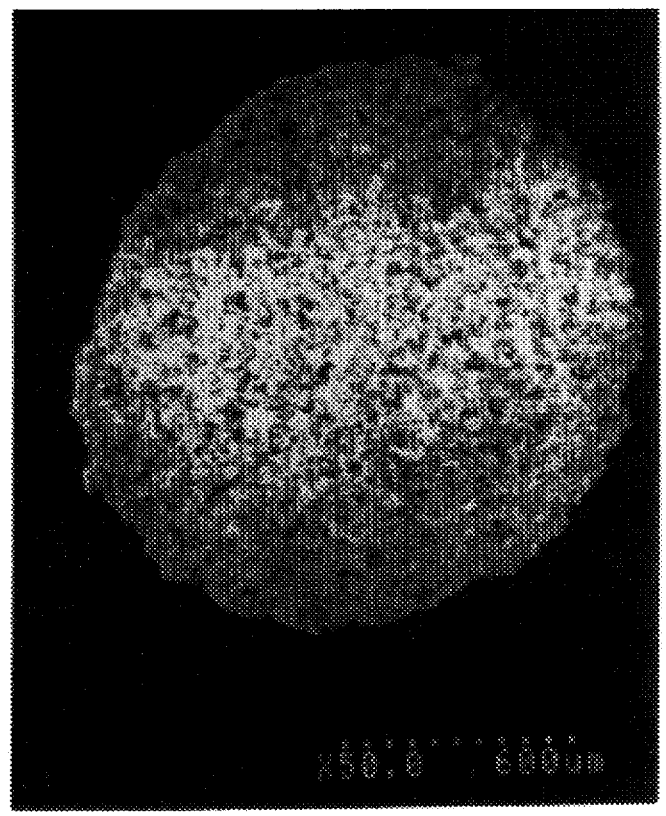
Figure 5:
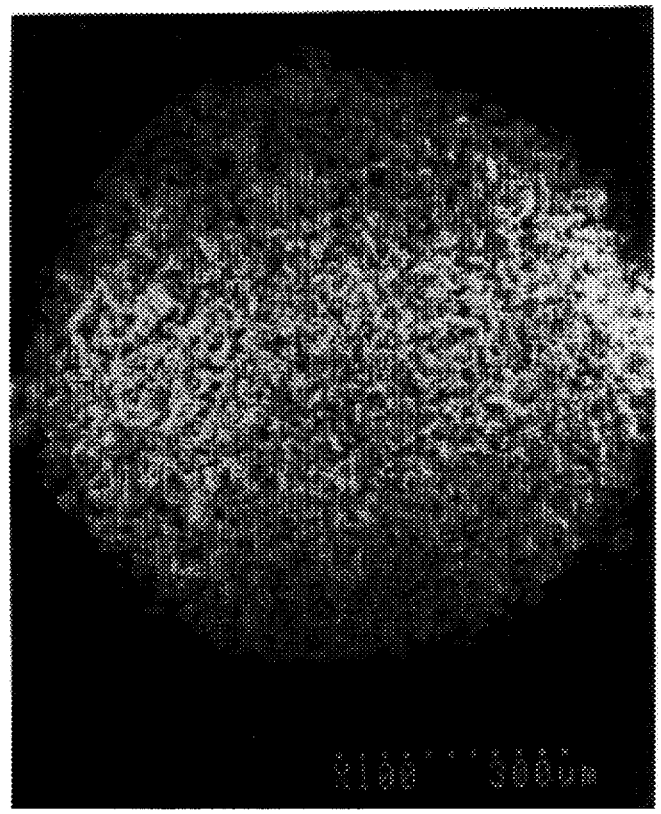

More particularly according to the present invention, in a preferred embodiment of the process aspect thereof, the coumarin and/or derivative thereof is melted, then the molten mass is extruded through a nozzle to form droplets. Said droplets are solidified by permitting them to fall by gravity in a tower against a countercurrent of cold gas, and the spherules obtained are next recovered.

The process of the invention is ideally suited for the preparation of coumarin spherules/beads and it is equally applicable to the derivatives of coumarin, provided they have a melting point of from 50° C. to 200° C., preferably from 50° C. to 100° C.

The present invention is especially well suited for the production of spherules/beads from coumarin compounds having the following structural formula (I):

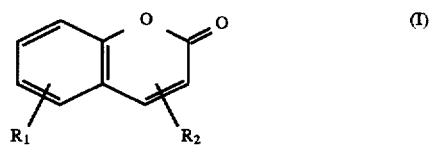

in which $R_1$ and $R_2$, which may be identical or different, are each a hydrogen atom, a linear or branched alkyl radical having from 1 to 4 carbon atoms, or a linear or branched alkoxy radical having from 1 to 4 carbon atoms.

The preferred compounds of formula (I) for the production of spherules are those wherein formula (I), $R^1$ and $R^2$, which may be identical or different, are each a hydrogen atom or a methyl or methoxy radical.

Specific examples of suitable compounds of formula (I) are:

Coumarin;

3-Methylcoumarin;

4-Methylcoumarin;

5-Methylcoumarin;

6-Methylcoumarin;

7-Methylcoumarin;

8-Methylcoumarin;

4-Methoxycoumarin;

4-Methyl-7-methoxycoumarin;

4-Methyl-7-ethoxycoumarin.

The term "coumarin" is intended as a generic expression which designates both coumarin and derivatives thereof having formula (I).

The spherules obtained in accordance with this invention have unique physicochemical properties.

The definitions and techniques for determining or measuring these physicochemical properties are more fully described below.

The dimensions or particle sizes are determined by screening through metal sieves.

The coumarin spherules are in the form of white beads. The particulates are substantially spherical, having a diameter which can be selected within a wide range using the process of the invention. Thus, the particle size can range from 100 μm to 2,000 μm, but preferably ranges from 300 μm to 1,000 μm.

In general, the dimensions of the particles, expressed as the average diameter ($d_{50}$), ranges from 300 μm to 2,000 μm, preferably from 500 μm to 1,500 μm, and more preferably from 700 μm to 1,200 μm. The average diameter is defined as that at which 50% by weight of the particles are of a diameter greater than or less than the average diameter.

FIGS. 1 to 5 are scanning electron photomicrographs which show the morphology of the coumarin spherule/bead obtained in accordance with the invention.

A uniform granulometric distribution was observed in the product obtained.

The density of the spherules can be predetermined by adapting or adjusting the parameters of the process. Hence, the quality of the final products can be adjusted depending on market demands. Thus, the bulk density (loosely packed) of the spherules can range from 0.25 and 0.8, preferably from 0.4 to 0.7.

The coumarin spherules of the invention have a compressive strength ranging from 500 to 10,000N/m$^2$, preferably from 1,000 to 5,000N/m$^2$, at a stress of less than 10,000N/m$^2$.

They have cohesive properties which provide good flow characteristics.

The invention thus features coumarin spherules which, because of their physical state, are attrition resistant, while retaining a rapid dissolution rate during use. The dissolution rate in ethanol, which constitutes a galenic test, is lower than the dissolution rate of the corresponding crystalline powder. More particularly, for coumarin itself the dissolution rate in ethanol of spherules thereof is less than 170 seconds, preferably ranging from 100 to 170 seconds, most preferably from 100 and 130 seconds.

The unique morphology of the beads of the invention is obtained using an ideally suitable production process.

The process for the production of coumarin spherules entails melting the coumarin and/or derivative thereof to the extent necessary, then fragmenting the molten mass into droplets and solidifying the resulting droplets in a gaseous cooling current, and recovering the solid spherules thus produced.

The process of the invention utilizes molten coumarin.

The molten coumarin can be supplied directly from a production line.

It is also possible to melt the coumarin. In this instance, the compound is heated to its melting point. Preferably, the compound is heated to a temperature which is slightly higher than its melting point, preferably at most 5° C. above its melting point. For coumarin itself, this temperature ranges from 70° C. to 75° C.

This operation is generally carried out with stirring.

In a subsequent step, the molten mass is transformed into droplets. This operation can be carried out using any fragmentation means, for example a flat nozzle with circular orifice(s).

In a preferred embodiment of the invention, the droplets are formed by passing the molten mass through an orifice, in particular by extrusion through a nozzle.

The following operation ensures the "freezing" of the droplets into spherules by contacting them with a cold gas, the temperature thereof advantageously ranging from −30° C. to 20° C., preferably from −20° C. to 10° C.

The cold gas is preferably air, but any gas may be used provided that it is inert vis-a-vis the coumarin. Nitrogen may be used, but, in general, air is preferred, preferably oxygen-depleted air (10%, for example).

The cold gas current preferably flows countercurrent to the material stream.

The residence time, which is the period of time between the formation of the droplet at the outlet of the nozzle and its transfer to the recovery system, advantageously ranges from 1 to 10 seconds, more preferably from 1 to 3 seconds.

One technique for attaining the desired residence time is to permit the droplets to fall by gravity in a tower against a countercurrent stream of cold gas, as described above.

At the end of the reaction, the spherules are recovered via any known means, for example by gravity in a recovery receptacle or, preferably, via a fluidized bed technique.

The coumarin spherules thus obtained have the characteristics and properties described above.

One very important advantage of the process of the invention is not only that a unique form of coumarin is provided, but also that the product has been subjected to purification. Indeed, it has been demonstrated that the concentration of impurities in the spherules is reduced compared with the starting powder. The differential thermal analysis curves shown in FIG. 6 (determined using Perkin-Elmer apparatus) evidence this phenomenon.

Figure 6:
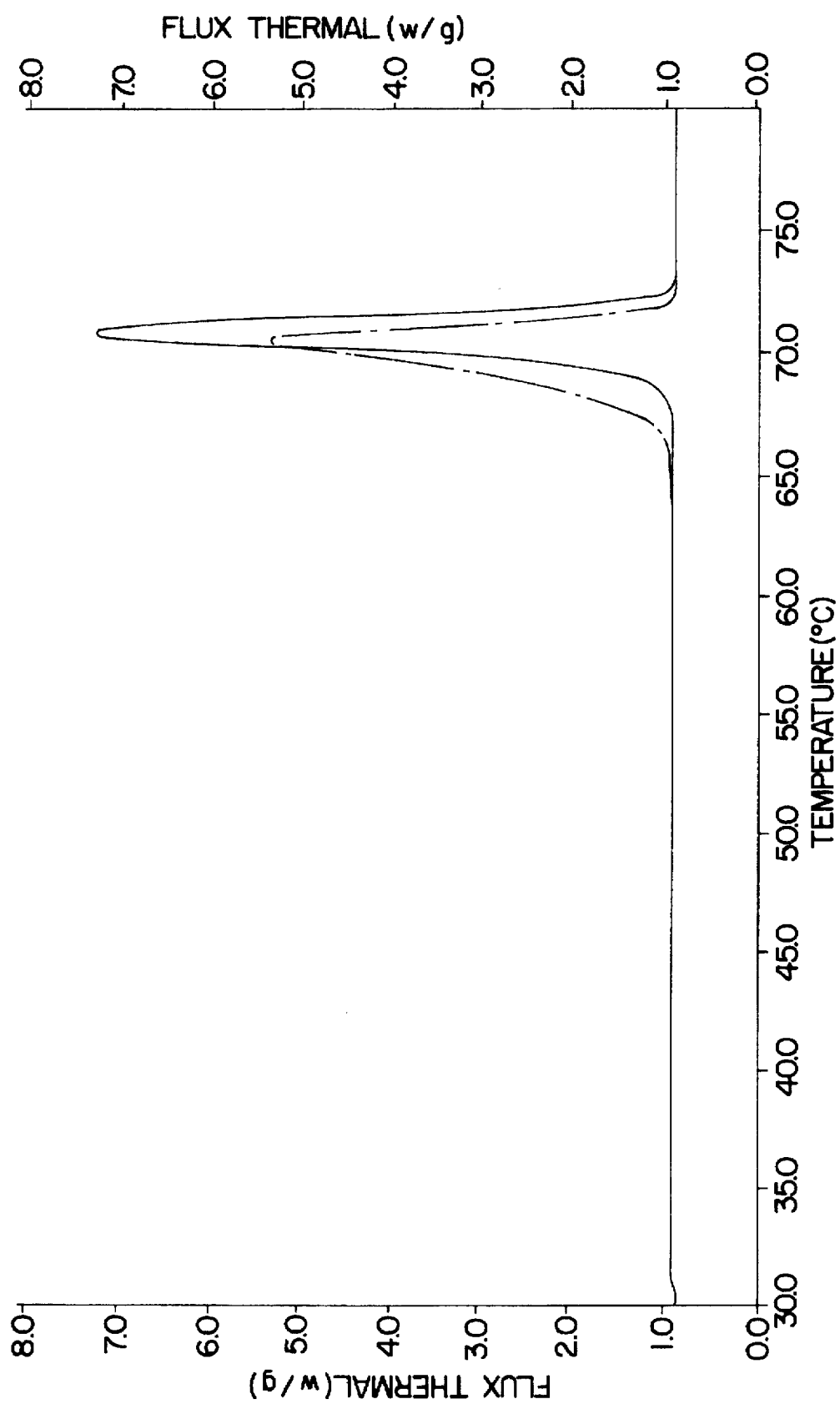
FIG. 6 is a graph plotting differential thermal analysis curves and demonstrating the greater purity of the solid coumarin spherules/beads of the invention.

FIG. 6 is a graph plotting two curves of the variation in thermal flux (expressed in w/g) as a function of melting point (expressed in °C.): curve (A) is the curve obtained using a commercially available coumarin in powder form, and curve (B) was obtained from coumarin prepared from the same starting power, but formed into spherules in accordance with the present invention.

The difference in the height of the peaks and the gradient of the front of curve (B) compared with curve (A) indicates that the coumarin formed in accordance with the invention is of higher purity.

In addition, it has been shown that when the cooling gas flows, as is preferable, countercurrently to the falling droplets and has a temperature of more than 10° C., spherules are obtained which have a dendritic morphology giving rise to a reduction in bulk density, generally to less than 0.35, and preferably ranging from 0.25 to 0.35. In this instance, the dissolution rate of the spherules is improved.

The apparatus used to carry out the process of the invention comprises two assemblies: a first assembly for forming the spherules and a second assembly for recovery of the spherules thus formed.

The first assembly comprises a storage receptacle which is preferably stirred when the coumarin emanates from a production line, or a melting kettle to melt the coumarin, and a vessel which is typically a tower, preferably 4 to 8 meters in height, comprising, at its upper end, means for fragmenting into droplets, preferably a nozzle, and one or more cold gaseous current inlets at its lower end, which transforms the base of the tower into a cooling zone.

The coumarin is introduced via a double-screw feed hopper into a melting kettle which is a reactor provided with a temperature regulation system, for example a double envelope or jacket, to maintain the coumarin in the molten state.

The nozzle can be a single-holed nozzle or a multi-holed nozzle in which the number of apertures can range from 1 to 100.

A system comprising a plurality of nozzles, for example two fixed nozzles in parallel, may be employed.

The diameter of the apertures in the nozzle depends on the spherule dimensions required. It can range from 100 to 1,000 μm, but preferably from 200 to 500 μm.

The size of the aperture is always less than the size of the spherule produced. Thus, a nozzle with apertures of about 200 μm would be used to produce spherules having an average diameter of 600 μm.

A static nozzle can be used, but it is possible to also use a nozzle which is electrically vibrated at high frequency, for example 500 to 10,000 hertz.

The molten compound is injected into the nozzle either by means of a positive displacement vacuum pump, or by means of an overpressure using a gaseous current, preferably a pressurized stream of nitrogen. The overpressure advantageously is 5% to 500% above atmospheric pressure.

The nozzle is typically maintained at a temperature ranging from 70° C. to 80° C.

It is possible, but not critical, to provide a gaseous current at the nozzle, preferably a concurrent of air with the jet exiting the nozzle. This air current is preferably at a temperature of from room temperature to 60° C. The gaseous concurrent improves the regularity of the spherule dimensions and prevents the droplets from coalescing.

Baffles and grids can be provided on the internal wall member of the central portion of the tower to homogenize the gaseous stream.

The current of cold gas is introduced at the base of the tower, preferably a stream of cold air to "freeze" the droplets into spherules. The air current is preferably at a temperature ranging from −30° C. to 20° C., preferably from −20° C. to 10° C.

The cold air preferably exits the tower below the nozzle at a distance of one-tenth of the total height of the cooling zone.

The spherule recovery system at the base of the tower can be constituted by a recovery receptacle, but it is preferable to employ means which fluidize the bed of particles. It comprises a receptacle, which is preferably cylindrical, having a grid at its lower end through which a gaseous current flows, preferably an oxygen-depleted stream of air. The air flow rate, which depends on the particle size, must be such that the particles are maintained in suspension. This could be, for example, 5 to 30 $m^3/h$ for a tower diameter of 80 mm.

In this zone of the apparatus, cooling is continued, since the air temperature is the same (±5° C.) as the temperature of the cold air stream at the base of the tower.

The fluidization means includes an outlet for evacuating the spherules.

In one embodiment of the invention, the apparatus illustrated in FIG. 7 of the accompanying drawings is used.

FIG. 7 is a schematic side view of an apparatus for carrying out the process of the invention.

The apparatus comprises two zones: the upper portion or prilling tower (A) and the lower portion which schematically includes a fluidization means (B).

The powdered coumarin is introduced into vessel 2: the second vessel 1 contains a washing solution (for example methanol) for the supply system at the end of the operation.

Nitrogen is admitted via line 5 at an overpressure into storage receptacles 1 or 2.

The tower is 4 meters high and includes a nozzle 4 in its upper end. A supply line 3 for a current of cold air is provided in the lower end thereof.

The cooling air introduced via line 3 exists through outlet 6 beneath the outlet of nozzle 4.

Baffles are provided at 8 in the central portion of the tower, as well as an annular grid to homogenize the air stream 9.

The lower end 8 of the tower, which is preferably tapered to facilitate spherule collection, is provided with a fluidization means comprising a cold air inlet 9 and an outlet 10 for evacuating the spherules obtained.

In order to further illustrate the present invention and the advantages thereof; the following specific examples are given, it being understood that same are intended only as illustrative and in nowise limitative.

In said examples to follow, the techniques described below were used to measure or determine the various characteristics and properties of the spherule final products:

Bulk density (loosely packed)

This was measured using the apparatus shown in FIG. 8.

First, the empty measuring cylinder 2 was weighed. The powder to be measured was then introduced into the measuring cylinder using funnel 1 until the level of the powder reached the 250 $cm^3$ mark (level A) on the measuring cylinder.

The mass of the powder was determined by weighing the full measuring cylinder. The measuring cylinder was fixed onto the support 3 by means of a clip 4.

The counter 8 was set at zero. The counter records the number of times the base of the measuring cylinder was struck.

The measuring cylinder was then subjected to vertical shocks applied to its base by a hammer 5 driven by a motor 6 via a cam 7. The operation was halted when the volume was constant (level B).

The change in the bulk volume indicated by the graduations on the measuring cylinder was recorded as a function of the number of hammer strokes.

An experimental settling curve was thus obtained.

Bulk volume=f(number of strikes) which is transformed into a curve of bulk density=f(number of strikes).

The bulk density is determined using the relationship:

bulk density=mass of powder introduced (g)/bulk volume ($cm^3$)

Compressive strength

The compressive strength (fc) of the products of the invention was measured in a Jenike cell using the technique described by L. Svarosvsky in "Powder Testing Guide: Methods of measuring the physical properties of bulk powders," Elsevier Applied Science, pp. 49–52 (1987).

Dissolution rate in ethanol x g of powder (spherules or crystalline powder) was dissolved in a test tube in ethanol at 25° C., with stirring, to a concentration of 0.02% by weight.

The evolution of UV absorbance of the solution was monitored (using a spectrophotometer) as a function of time. The dissolution rate, expressed in seconds, was obtained when the absorbance stabilized at its final value.

EXAMPLES

The procedure employed in the following examples will now be described:

2,000 g of crystalline coumarin in powder form having the following characteristics were used:

(a) bulk density (loosely packed)=0.683;

(b) dissolution rate in ethanol=174 s.

The process of the invention was carried out using the apparatus described above and illustrated in FIG. 7.

The nozzle, which could be vibrated, had the characteristics described in the following examples.

Coumarin powder was introduced into vessel 2, vessel 1 containing a wash solution for the supply system (methanol).

Coumarin was melted in the melting kettle by heating with hot water circulating in the double jacket. The product temperature was 75° C. at 2 and 71° C. at 4, at the nozzle outlet. The product flow rate will be more fully described below.

Cooling air was introduced via line 3 at a flow rate of 1,000 $m^3/h$, i.e., a speed of 0.7 m/s in the tower. The air was removed via outlet 6.

The air temperatures at the tower inlet 3 and at its outlet 6 are reported in Tables accompanying each Example.

Similarly, the temperature of the fluidization air at inlet 9 is also reported in each Table.

The spherules obtained were collected at base 8 and recovered via outlet 10.

Example 1

1. Coumarin spherules were prepared in an apparatus as shown in FIG. 7, having seven apertures, each aperture having a diameter of 250 μm. The ratio L/D was 1; L represents the orifice length and D represents the orifice diameter.

The procedure used was as described above; the operating conditions are reported in Table I below:

TABLE I:

| | |
|---|---|
| Nozzle 4 vibration frequency, hertz | 1,160 |
| Nitrogen overpressure, bars, at nozzle 4 | 0.202 |
| Product flow rate at nozzle 4 outlet, kg/h | 5.60 |
| Air temperature at tower inlet 3, °C. | −10° C. |
| Air temperature at tower outlet 6, °C. | −6° C. |
| Air temperature of fluidized bed 9, °C. | −5°C. |

After 12 minutes of operation, 840 g of spherules were recovered, having an average diameter ($d_{50}$) of 800 μm.

2. The photomicrograph shown in FIG. 1, taken with a microscope (M=100), evidenced that the coumarin obtained had a bead-like morphology.

The other physicochemical properties were as follows:

(a) bulk density (loosely packed)=0.47;

(b) dissolution rate in ethanol=125 s.

Example 2

1. The coumarin spherules were prepared as described in Example 1; the modifications to the parameters of the process are reported in the following Table II:

TABLE II:

| | |
|---|---|
| Nozzle 4 vibration frequency, hertz | 5,600 |
| Nitrogen overpressure, bars, at nozzle 4 | 0.222 |
| Product flow rate at nozzle 4 outlet, kg/h | 5.60 |
| Air temperature at tower inlet 3, °C. | 10 |
| Air temperature at tower outlet 6, °C. | 11 |
| Air temperature of fluidized bed 9, °C. | 10 |

After 9 minutes of operation, 410 g of coumarin spherules were recovered having an average diameter ($d_{50}$) of 700 μm.

2. The product obtained had the morphology shown in FIG. 2 (M=100), and had the following properties:

(a) bulk density (loosely packed)=0.43;

(b) dissolution rate in ethanol=130 s.

Example 3

Figure 7:
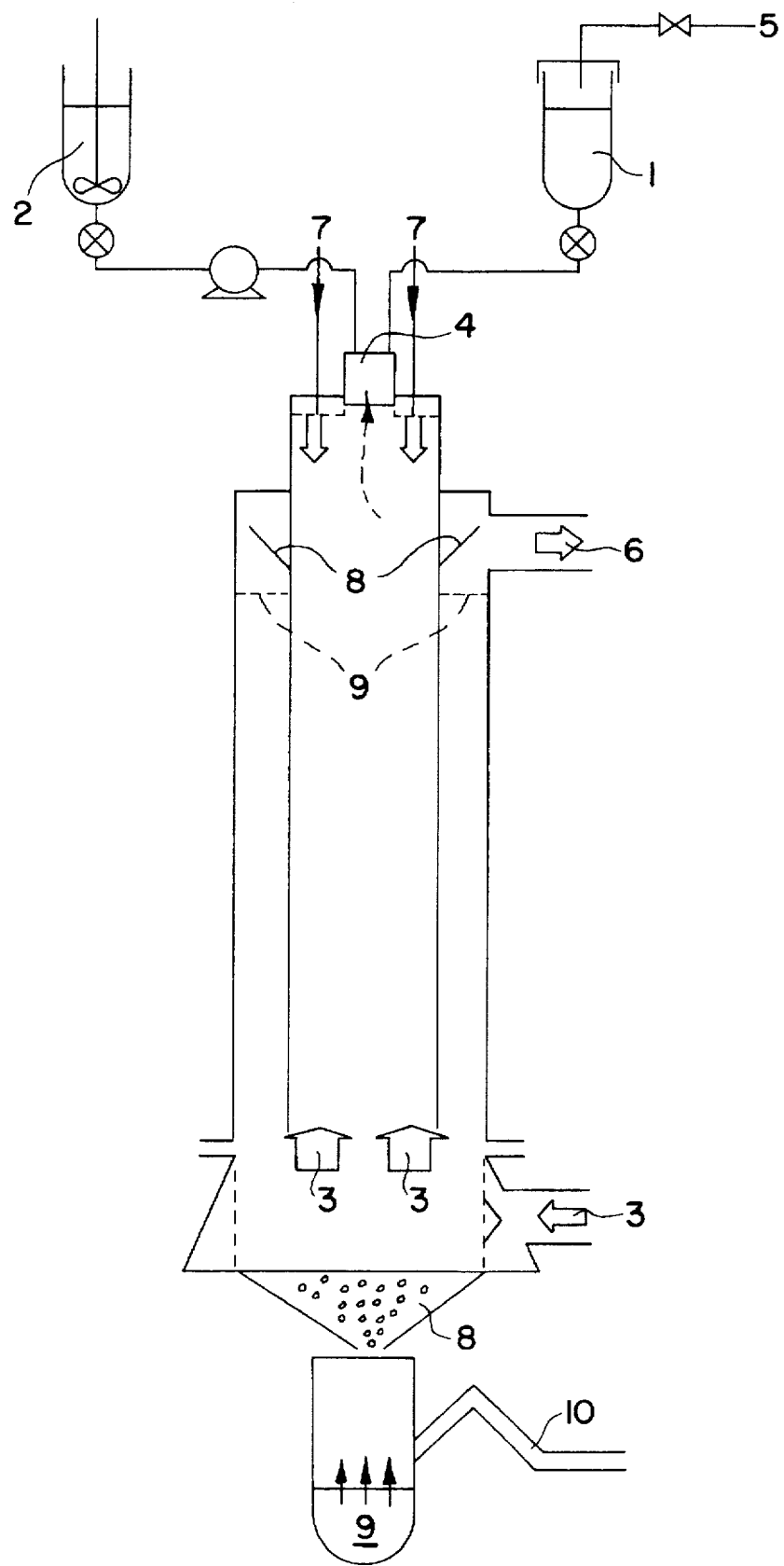
FIG. 7 is a schematic/diagrammatic cross-sectional view of apparatus suitable for preparing the spherules/beads according to this invention.
Figure 8:
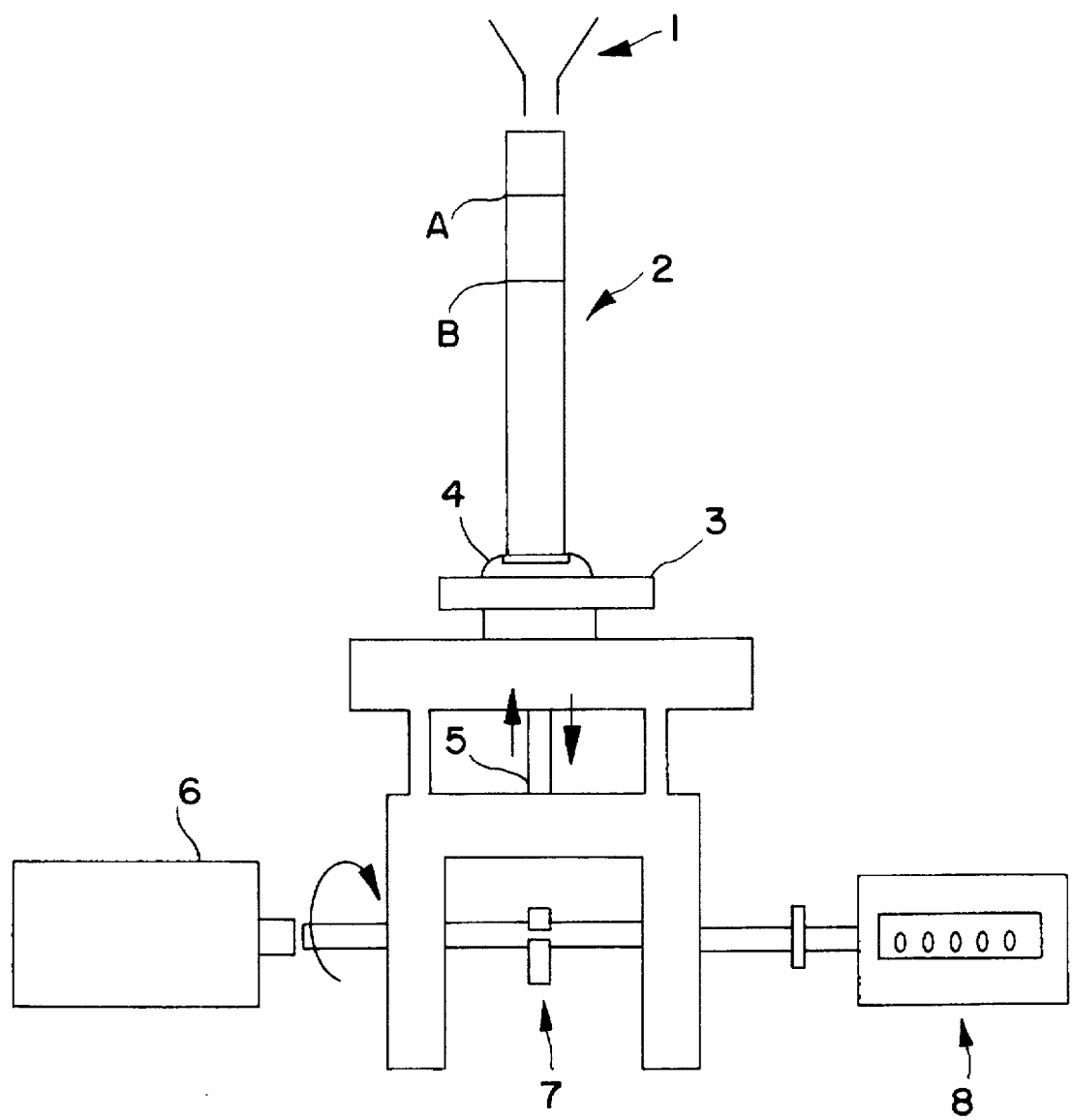
FIG. 8 is a schematic/diagrammatic view of apparatus suitable for measuring the bulk density of the spherules/beads of the invention.

1. Coumarin spherules were prepared in an apparatus as shown in FIG. 7, comprising a nozzle having seven apertures, each aperture having a diameter of 400 μm, the ratio L/D was 3.

The procedure used was as described above; the operating conditions are reported in Table III below:

TABLE III:

| | |
|---|---|
| Nozzle 4 vibration frequency, hertz | 1,540 |
| Nitrogen overpressure, bars, at nozzle 4 | 0.08 |
| product flow rate at nozzle 4 outlet, kg/h | 7.00 |
| Air temperature at tower inlet 3, °C. | 12 |
| Air temperature at tower outlet 6, °C. | 13 |
| Air temperature of fluidized bed 9, °C. | 10 |

After 12 minutes of operation, 910 g of spherules were recovered having an average diameter ($d_{50}$) of 1,130 μm.

2. The product obtained had the dendritic morphology shown in FIG. 3 (M=60), and had the following properties:

(a) bulk density (loosely packed)=0.27;

(b) compressive strength (fc)=1.6 kN/m² at a pressure of 4.8 kN/m².

(c) dissolution rate in ethanol=104 s.

Example 4

1. Coumarin spherules were prepared as described in Example 3; the modifications to the parameters of the process are reported in Table IV below:

TABLE IV:

| | |
|---|---|
| Nozzle 4 vibration frequency, hertz | 800 |
| Nitrogen overpressure, bars, at nozzle 4 | 0.075 |
| product flow rate at nozzle 4 outlet, kg/h | 7.00 |
| Air temperature at tower inlet 3, °C. | −10° C. |
| Air temperature at tower outlet 6, °C. | −6° C. |
| Air temperature of fluidized bed 9, °C. | −10°C. |

After 10 minutes of operation, 840 g of spherules were recovered having an average diameter ($d_{50}$) of 910 μm.

2. The product obtained had the morphology shown in FIG. 4 (M=50), and had the following properties:

(a) bulk density (loosely packed)=0.50;

(b) compressive strength (fc)=1.25 kN/m² at a pressure of 4.8 kN/m².

(c) dissolution rate in ethanol=120 s.

Example 5

1. The procedure of Example 4 was repeated, the only difference being that the nozzle was static.

After 8 minutes of operation, 520 g of coumarin spherules were obtained having an average diameter ($d_{50}$) of 850 μm.

2. The product obtained had the morphology shown in FIG. 5 (M=100). A slight difference in granulometric distribution was seen, as the product appeared to be less uniform.

The physicochemical properties of the spherules were as follows:

(a) bulk density (loosely packed)=0.47.

Example 6

1. The coumarin spherules were prepared as described in Example 1; the modifications to the parameters of the process are reported in Table V:

TABLE V:

| | |
|---|---|
| Nozzle 4 vibration frequency, hertz | 1,990 |
| Nitrogen overpressure, bars, at nozzle 4 | 0.080 |
| product flow rate at nozzle 4 outlet, kg/h | 4.00 |
| Air temperature at tower inlet 3, °C. | 10 |
| Air temperature at tower outlet 6, °C. | 12 |
| Air temperature of fluidized bed 9, °C. | 6 |

2. The product obtained had the following properties:
(a) bulk density (loosely packed)=0.49;
(b) dissolution rate in ethanol=160 s.

Example 7

1. The procedure of Example 6 was repeated, the only difference being that the nozzle was static.

The product obtained had the following properties:
(a) bulk density (loosely packed)=0.45;
(b) dissolution rate in ethanol=135 s.

Example 8

1. The coumarin spherules were prepared as described in Example 1; the modifications to the parameters of the process are reported in the following Table VI:

TABLE VI

| | |
|---|---|
| Nozzle 4 vibration frequency, hertz | 1,990 |
| Nitrogen overpressure, bars, at nozzle 4 | 0.075 |
| product flow rate at nozzle 4 outlet, kg/h | 3.42 |
| Air temperature at tower inlet 3, °C. | 12 |
| Air temperature at tower outlet 6, °C. | 14 |
| Air temperature of fluidized bed 9, °C. | 15 |

2. The product obtained had the following properties:
(a) bulk density (loosely packed)=0.42;
(b) dissolution rate in ethanol=142 s.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Particulates comprising free-flowing, non-agglomerating and attrition resistant, substantially spherical solid beads/spherules of a coumarin compound.

2. The bead/spherule particulates as defined by claim 1, said coumarin compound having a melting point ranging from 50° to 200° C.

3. The bead/spherule particulates as defined by claim 2, said coumarin compound having a melting point ranging from 50° to 100° C.

4. The bead/spherule particulates as defined by claim 1, said coumarin compound having the structural formula (I):

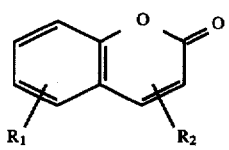

in which $R_1$ and $R_2$, which may be identical or different, are each a hydrogen atom, a linear or branched alkyl radical having from 1 to 4 carbon atoms, or a linear or branched alkoxy radical having from 1 to 4 carbon atoms.

5. The bead/spherule particulates as defined by claim 4, wherein formula (I), $R_1$ and $R_2$, which may be identical or different, are each a hydrogen atom or a methyl or methoxy radical.

6. The bead/spherule particulates as defined by claim 4, wherein formula (I), $R_1$ and $R_2$ are each a hydrogen atom.

7. The bead/spherule particulates as defined by claim 1, having a particle size ranging from 100 μm to 2,000 μm.

8. The bead/spherule particulates as defined by claim 7, having a particle size ranging from 300 μm to 1,000 μm.

9. The bead/spherule particulates as defined by claim 1, having a particle size, expressed as the average diameter ($d_{50}$), ranging from 300 μm to 2,000 μm.

10. The bead/spherule particulates as defined by claim 9, said average diameter ($d_{50}$) ranging from 500 μm to 1,500 μm.

11. The bead/spherule particulates as defined by claim 10, said average diameter ($d_{50}$) ranging from 700 m to 1,200 μm.

12. The bead/spherule particulates as defined by claim 1, having a loose bulk density ranging from 0.25 to 0.8.

13. The bead/spherule particulates as defined by claim 12, having a loose bulk density ranging from 0.4 to 0.7.

14. The bead/spherule particulates as defined by claim 1, having a compressive strength ranging from to 10,000N/m² at a stress of less than 10,000 N/m².

15. The bead/spherule particulates as defined by claim 14, having a compressive strength ranging from 1,000 to 5,000 N/m² at a stress of less than 10,000 N/m².

16. The bead/spherule particulates as defined by claim 1, having a dissolution rate in ethanol less than that of the corresponding crystalline powder.

17. The bead/spherule particulates as defined by claim 16, having a dissolution rate in ethanol no greater than 170 seconds.

18. The bead/spherule particulates as defined by claim 17, having a dissolution rate in ethanol of from 100 to 170 seconds.

19. The bead/spherule particulates as defined by claim 18, having a dissolution rate in ethanol of from 100 to 130 seconds.

20. A process for the preparation of the bead/spherule particulates as defined by claim 1, comprising prilling/fragmenting a melt of said coumarin compound into a stream of a cooling gas, thereby solidifying the droplets thereof, and recovering the solid beads/spherules thus produced.

21. The process as defined by claim 20, comprising prilling/fragmenting said melt by extrusion through a nozzle.

22. The process as defined by claim 21, said cooling gas flowing countercurrently to said droplets.

23. The process as defined by claim 22, said droplets falling by gravity in a tower.

24. The process as defined by claim 23, said nozzle having up to 100 outlet apertures.

25. The process as defined by claim 24, said apertures having a diameter ranging from 100 to 1,000 µm.

26. The process as defined by claim 25, said apertures having a diameter ranging from 200 to 600 µm.

27. The process as defined by claim 21, said nozzle being a static nozzle electrically vibrated at high frequency.

28. The process as defined by claim 23, said cooling gas comprising oxygen-depleted air at a temperature ranging from −30° to 20° C.

29. The process as defined by claim 23, the residence time of the droplets from nozzle to recovery ranging from 1 to 10 seconds.

30. The process as defined by claim 23, comprising recovering said solid beads/spherules via fluidized bed technique.

* * * * *